United States Patent [19]
Coulie et al.

[11] Patent Number: 5,846,826
[45] Date of Patent: Dec. 8, 1998

[54] ISOLATED CYTOLYTIC T CELL LINE SPECIFIC TO COMPLEXES OF HLA-B44 MOLECULES AND SPECIFIC NONAPEPTIDES

[75] Inventors: Pierre Coulie; Thierry Boon-Falleur, both of Brussels, Belgium

[73] Assignee: Ludwig Institute for Cancer Research, New York, N.Y.

[21] Appl. No.: 611,273

[22] Filed: Mar. 5, 1996

Related U.S. Application Data

[62] Division of Ser. No. 253,503, Jun. 3, 1994, Pat. No. 5,589,334.

[51] Int. Cl.⁶ .............................. C12N 5/02; A61K 39/00; C07K 7/06
[52] U.S. Cl. ..................... 435/372.3; 514/15; 530/403; 530/328; 424/185.1; 424/193.1
[58] Field of Search .............................. 435/240.1, 372.3; 514/15; 530/403, 528; 424/185.1, 193.1

[56] References Cited

U.S. PATENT DOCUMENTS 5,342,774  8/1994  Boon et al. .
5,519,117  5/1996  Wolfel .

OTHER PUBLICATIONS

Khanna et al 1992 J. Exp. Med. 176:169.
Van der Bruggen et al., "A Gene Encoding an Antigen Recognized by Cytolytic T Lymphocytes On a Human Melanoma", Science 254: 1643–1647 (Dec. 1991).
Khanna et al., "Localization of Epstein–Barr Virus Cytotoxic T Cell Epitopes Using Recombinant Vaccinia: Implications for Vaccine Development", J. Exp. Med. 176: 169–176 (Jul. 1992).

*Primary Examiner*—Thomas M. Cunningham
*Assistant Examiner*—Martha Lubet
*Attorney, Agent, or Firm*—Felfe & Lynch

[57] ABSTRACT

The invention involves cytolytic T cell lines which are specific for complexes of HLA-B44 molecules and nonamers which bind to these.

1 Claim, 4 Drawing Sheets

ISOLATED CYTOLYTIC T CELL LINE SPECIFIC TO COMPLEXES OF HLA-B44 MOLECULES AND SPECIFIC NONAPEPTIDES

This application is a Divisional of Ser. No. 08/253,503 filed Jun. 3, 1994 U.S. Pat. No. 5,589,334.

FIELD OF THE INVENTION

This invention relates to isolated peptides, derived from tumor rejection antigen precursors and presented by HLA-A2 and HLA-B44 molecules and uses thereof. In addition, it relates to the ability to identify those individuals diagnosed with conditions characterized by cellular abnormalities whose abnormal cells present complexes of these peptides and HLA-B44, the presented peptides, and the ramifications thereof. Also a part of the invention are the nucleic acid molecules which code for the tumor rejection antigen precursor, the tumor rejection antigen, and uses thereof.

BACKGROUND AND PRIOR ART

The process by which the mammalian immune system recognizes and reacts to foreign or alien materials is a complex one. An important facet of the system is the T cell response. This response requires that T cells recognize and interact with complexes of cell surface molecules, referred to as human leukocyte antigens ("HLA"), or major histocompatibility complexes ("MHCs"), and peptides. The peptides are derived from larger molecules which are processed by the cells which also present the HLA/MHC molecule. See in this regard Male et al., *Advanced Immunolocry* (J. P. Lipincott Company, 1987), especially chapters 6–10. The interaction of T cell and complexes of HLA/peptide is restricted, requiring a T cell specific for a particular combination of an HLA molecule and a peptide. If a specific T cell is not present, there is no T cell response even if its partner complex is present. Similarly, there is no response if the specific complex is absent, but the T cell is present. This mechanism is involved in the immune system's response to foreign materials, in autoimmune pathologies, and in responses to cellular abnormalities. Recently, much work has focused on the mechanisms by which proteins are processed into the HLA binding peptides. See, in this regard, Barinaga, Science 257: 880 (1992); Fremont et al., Science 257: 919 (1992); Matsumura et al., Science 257: 927 (1992); Latron et al., Science 257: 964 (1992).

The mechanism by which T cells recognize cellular abnormalities has also been implicated in cancer. For example, in PCT application PCT/US92/04354, filed May 22, 1992, published on Nov. 26, 1992, and incorporated by reference, a family of genes is disclosed, which are processed into peptides which, in turn, are expressed on cell surfaces, which can lead to lysis of the tumor cells by specific CTLs. The genes are said to code for "tumor rejection antigen precursors" or "TRAP" molecules, and the peptides derived therefrom are referred to as "tumor rejection antigens" or "TRAs". See Traversari et al., Immunogenetics 35: 145 (1992); van der Bruggen et al., Science 254: 1643 (1991), for further information on this family of genes.

In U.S. patent application Ser. No. 938,334, the disclosure of which is incorporated by reference, nonapeptides are taught which bind to the HLA-A1 molecule. The reference teaches that given the known specificity of particular peptides for particular HLA molecules, one should expect a particular peptide to bind one HLA molecule, but not others. This is important, because different individuals possess different HLA phenotypes. As a result, while identification of a particular peptide as being a partner for a specific HLA molecule has diagnostic and therapeutic ramifications, these are only relevant for individuals with that particular HLA phenotype. There is a need for further work in the area, because cellular abnormalities are not restricted to one particular HLA phenotype, and targeted therapy requires some knowledge of the phenotype of the abnormal cells at issue.

The enzyme tyrosinase catalyzes the reaction converting tyrosine to dehydroxyphenylalanine or "DOPA" and appears to be expressed selectively in melanocytes (Muller et al., EMBOJ 7: 2715 (1988)). An early report of cDNA for the human enzyme is found in Kwon, U.S. Pat. No. 4,898,814. A later report by Bouchard et al., J. Exp. Med. 169: 2029 (1989) presents a slightly different sequence. A great deal of effort has gone into identifying inhibitors for this enzyme, as it has been implicated in pigmentation diseases. Some examples of this literature include Jinbow, WO9116302; Mishima et al., U.S. Pat. No. 5,077,059, and Nazzaropor, U.S. Pat. No. 4,818,768. The artisan will be familiar with other references which teach similar materials.

U.S. patent application Ser. No. 08/081,673, U.S. Pat. No. 5,487,974 filed Jun. 23, 1993 and incorporated by reference, teaches that tyrosinase may be treated in a manner similar to a foreign antigen or a TRAP molecule—i.e., it was found that in certain cellular abnormalities, such as melanoma, tyrosinase is processed and a peptide derived therefrom forms a complex with HLA molecules on certain abnormal cells. These complexes were found to be recognized by cytolytic T cells ("CTLs"), which then lyse the presenting cells. The ramifications of this surprising and unexpected phenomenon were discussed. Additional peptides have now been found which also act as tumor rejection antigens presented by HLA-A2 molecules. These are described in Ser. No. 08/203,054, filed Feb. 28, 1994 and incorporated by reference.

U.S. patent application Ser. No. 08/233,305 U.S. Pat. No. 5,519,119 filed Apr. 26, 1994 and incorporated by reference, disclosed that tyrosinase is also processed to an antigen presented by HLA-B44 molecules. The finding was of importance, because not all individuals are HLA-A2$^+$. The fact that tyrosinase is processed to an HLA-B44 presented peptide, however, does not provide for a universal approach to diagnosis and treatment of all HLA-B44$^+$ tumors, because tyrosinase expression is not universal. Further, the fact that tyrosinase is expressed by normal cells as well as tumor cells may suggest some caution in the therapeutic area.

It has now been found that a non-tyrosinase coding gene also expresses a tumor rejection antigen precursor which is processed to at least one tumor rejection antigen presented by HLA-B44 molecules. This, inter alia, is the subject of the invention disclosure which follows.

BRIEF DESCRIPTION OP THE FIGURES

FIGS. 1A–C show the results of chromium release assays using each of three different cell lines (LB33-MELc1, LB33 EBV-B, and K562), and cytolytic T cell clone 159/5. The data are presented in terms of effector/target ratios vs % of lysis.

FIG. 2 shows the result of lysis studies which identified cell variants "A$^-$" "B$^-$", and "A$^-$,B$^-$". Again, a chromium release assay was used. Cell line LB33-MELc1 is A$^+$B$^+$, as is indicated by the positive lysis with both CTL lines tested. CTL 159/93 is anti-A, while CTL 159/5 is anti-B.

FIG. 3 shows results obtained when the variant A⁻B⁻ was transfected with coding sequences for each of HLA-A28, HLA-B44, and HLA-Cw7, as compared to a control line. The results are depicted in terms of the sensitive TNF release assay (pg/ml), where CTL 159/5 was used.

FIGS. 4A–B show TNF release by CTL 195/5, where COS cells were transfected with HLA-B44, or HLA-B44 plus a nucleic acid molecule in accordance with this invention.

DETAILED DESCRIPTION OF PREFERRED EMBODIMENTS

EXAMPLE 1

Melanoma cell line LB33-MEL which has been available to researchers for many years, was used in the following experiments. A clone derived therefrom was also used. The clone is referred to hereafter as LB33-MELc1.

Samples containing mononuclear blood cells were taken from patient LB33. The melanoma cell line was contacted to the mononuclear blood cell containing samples. The mixtures were observed for lysis of the melanoma cell lines, this lysis indicating that cytolytic T cells ("CTLs") specific for a complex of peptide and HLA molecule presented by the melanoma cells were present in the sample.

The lysis assay employed was a chromium release assay following Herin et al., Int. J. Cancer 39:390–396 (1987), the disclosure of which is incorporated by reference. The assay, however, is described herein. The target melanoma cells were grown in vitro, and then resuspended at $10^7$ cells/ml in DMEM, supplemented with 10 mM HEPES and 30% FCS (i.e., from fetal calf serum) and incubated for 45 minutes at 37° C. with 200 μCi/ml of Na($^{51}$Cr)O₄. Labelled cells were washed three times with DMEM, supplemented with 10 mM Hepes. These were then resuspended in DMEM supplemented with 10 mM Hepes and 10% FCS, after which 100 ul aliquots containing $10^3$ cells, were distributed into 96 well microplates. Samples of PBLs were added in 100 ul of the same medium, and assays were carried out in duplicate. Plates were centrifuged for 4 minutes at 100 g, and incubated for four hours at 37° C. in a 5.5% CO₂ atmosphere.

Plates were centrifuged again, and 100 ul aliquots of supernatant were collected and counted. Percentage of $^{51}$Cr release was calculated as follows:

$$\% \ ^{51}Cr \ release = \frac{(ER - SR)}{(MR - SR)} \times 100$$

where ER is observed, experimental $^{51}$Cr release, SR is spontaneous release measured by incubating $10^3$ labeled cells in 200 ul of medium alone, and MR is maximum release, obtained by adding 100 ul 0.3% Triton X-100 to target cells.

Those mononuclear blood samples which showed high CTL activity were expanded and cloned via limiting dilution, and were screened again, using the same methodology.

The same method was used to test target K562 cells. When EBV-B cells were used, the only change was the replacement of DMEM medium by Hank's medium, supplemented with 5% FCS.

Figure 1C:
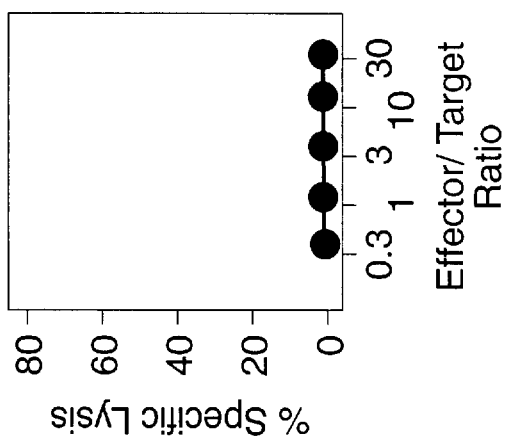
Figure 1B:
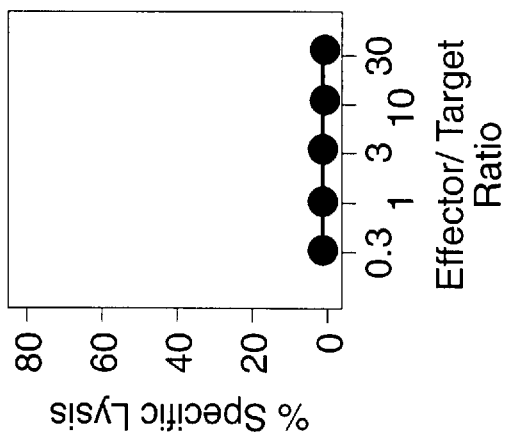
Figure 1A:
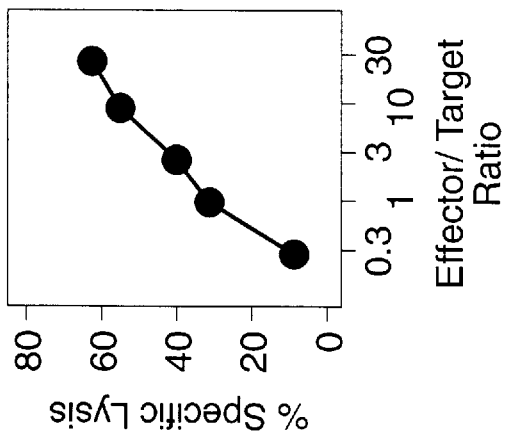

These experiments led to isolation of CTL clones LB33-CTL-159/5. FIG. 1 shows that this clone lysed tumor cells, but not EBV-B cells, or K562 cells.

Following the same protocol, a second CTL clone, i.e., LB33-CTL-159.3 was isolated. These lines will be referred to as "159/5" and "159/3", respectively. This second CTL has specificity differing from 159/5. This was ascertained following isolation of two antigen loss variants which (i) are lysed by 159/5 but not 159/3 and (ii) are not lysed by 159/5 and are lysed by 159/3. These variants are referred to as A⁻ and B⁻, respectively.

Figure 2:
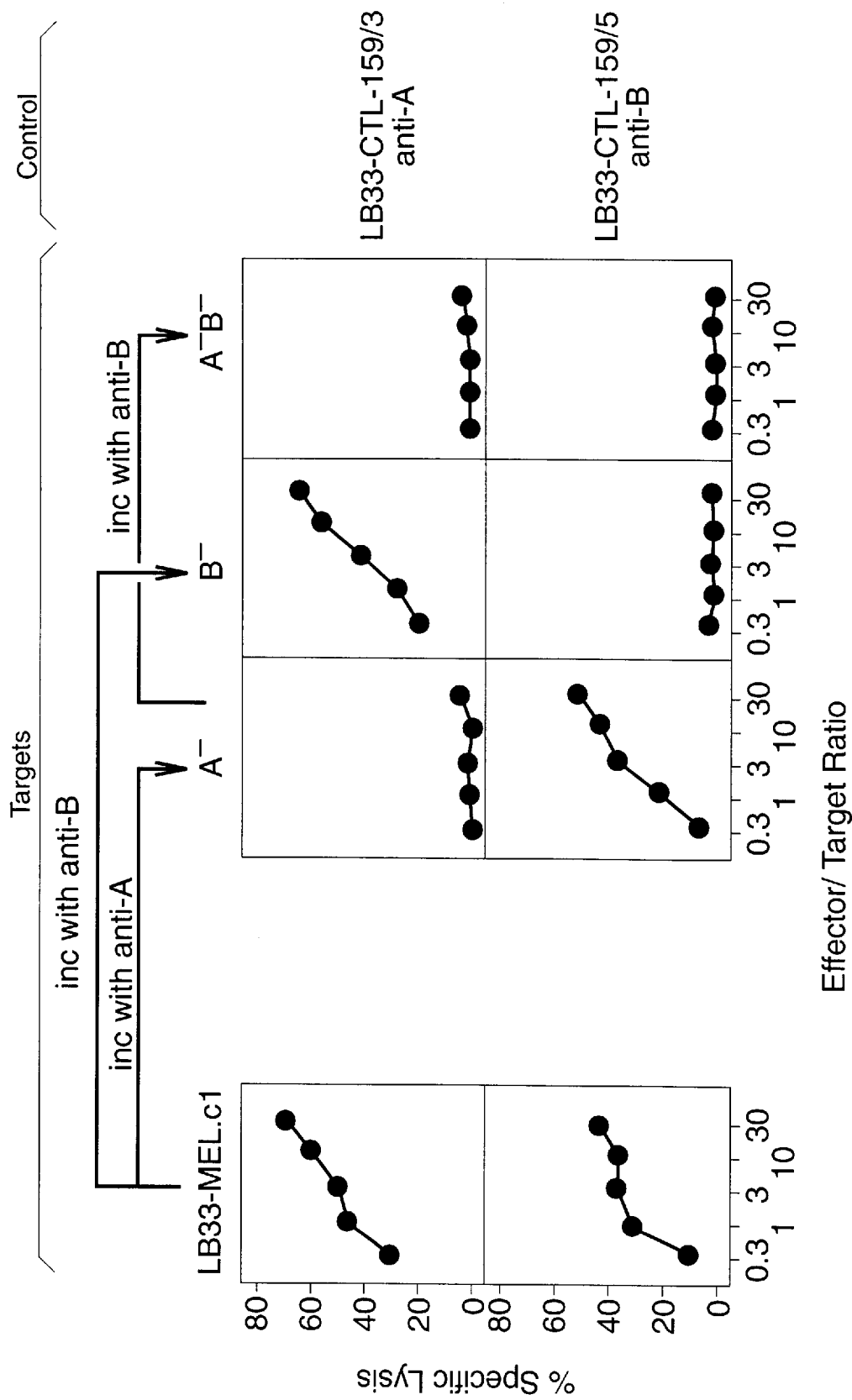

The A⁻ variant was then immunoselected with 159/5, and a third variant was obtained, which was not lysed by either 195/5 or 159/3. This variant is referred to as A⁻B⁻. FIG. 2 summarizes the results of the lysis assays, leading to isolation of the variants.

EXAMPLE 2

It was of interest to determine the pattern of HLA expression of variant A⁻B⁻. The patient from whom parent line LB33-MEL was derived was typed as HLA-A24, A28, B13, B44, Cw6, Cw7. When PCR expression analysis was carried out, it was found that both LB33-MELc1, and the B⁻ variant express all six alleles; however, the A⁻B⁻ variant does not express HLA-A28, B44, and Cw7. As a result, it was concluded that one of these HLA molecules presents the antigen leading to lysis by CTLs. The following example explores this further.

EXAMPLE 3

Figure 3:
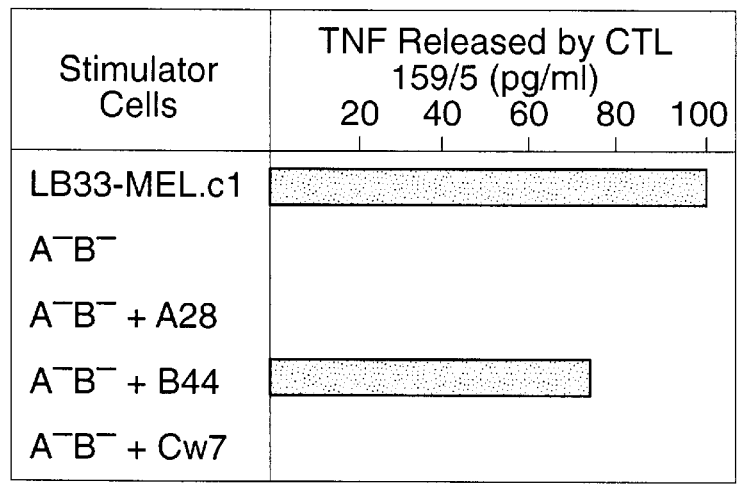

Samples of the A⁻B⁻ variant were transfected by plasmid pcDNA-I/AmpI which had cloned therein, one of HLA-A28, HLA-B44, or HLA-Cw7. Following selection, the cells were tested in a TNF release assay, following Traversari, et al., Immunogenetics 35: 145–152 (1992), incorporated by reference herein. The results are summarized in FIG. 3, which shows that HLA-B44 is clearly implicated in the presentation of the antigen.

EXAMPLE 4

Once the presenting HLA molecule was identified, studies were carried out to identify the molecule, referred to hereafter as the "tumor rejection antigen precursor" or "TRAP" molecule which was the source of the presented peptide.

To do this, total mRNA was isolated from cell line LB33-MELc1. The RNA was isolated using an oligo-dT binding kit, following well recognized techniques. Once the total mRNA was secured, it was transcribed into cDNA, again using standard methodologies. The cDNA was then ligated to EcoRI adaptors and cloned into the EcoRI site of plasmid pcDNA-I/Amp, in accordance with manufacturer's instructions. The recombinant plasmids were then electrophorated into DH5d E. coli (electroporation conditions: 1 pulse at 25 μfarads, 2500 V).

The transfected bacteria were selected with ampicillin (50 μg/ml), and then divided into pools of 100 bacteria each. Each pool represented about 50 different cDNAs, as analysis showed that about 50% of plasmids contained an insert. Each pool was amplified to saturation, and plasmid DNA was isolated via alkaline lysis, potassium acetate precipitation and phenol extraction, following Maniatis et al., in Molecular Cloning: A Laboratory Manual (Cold Spring Harbor, N.Y., 1982). Cesium gradient centrifugation was not used.

The amplified plasmids were then transfected into eukaryotic cells. Samples of COS-7 cells were seeded, at 15,000 cells/well into tissue culture flat bottom microwells, in Dulbeco's modified Eagles Medium ("DMEM") supplemented with 10% fetal calf serum. The cells were incubated overnight at 37° C., medium was removed and then replaced by 30 μl/well of DMEM medium containing 10% Nu serum, 400 μg/ml DEAE-dextran, 100 μM chloroquine, and 100 ng of a plasmid containing cDNA for HLA-B44 from LB33. Following four hours of incubation at 37° C., the medium was removed, and replaced by 50 μl of PBS containing 10% DMSO. This medium was removed after two minutes and replaced by 200 μl of DMEM supplemented with 10% of FCS.

Following this change in medium, COS cells were incubated for 48 hours at 37° C. Medium was then discarded, and 2000 cells of 159/5 were added, in 100 μl of Iscove's medium containing 10% pooled human serum 25 μ/ml IL-2. Supernatant was removed after 24 hours, and TNF content was determined in an assay on WEHI cells, as described by Traversari et al., Immunogenetics 35: 145–152 (1992), the disclosure of which is incorporated by reference. One pool stimulated TNF release above background, and these bacteria were cloned, and used in the following experiment.

EXAMPLE 5

Figure 4A:
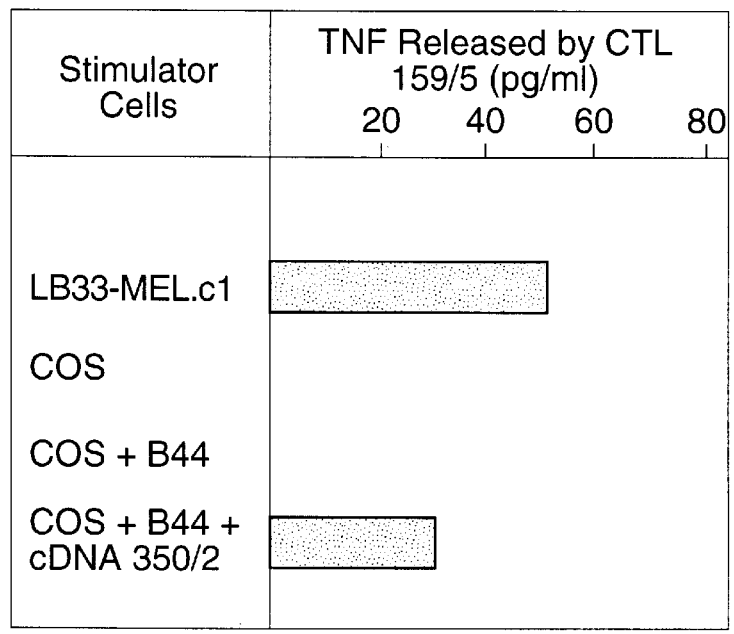

Plasmid DNA was extracted from the bacteria cloned in Example 4, transfected into a new sample of COS cells in the same manner as described supra, and the cells were again tested for stimulation of 159/5. A positive clone was found in clone 350/2, as demonstrated by data summarized in FIG. 4A.

Figure 4B:
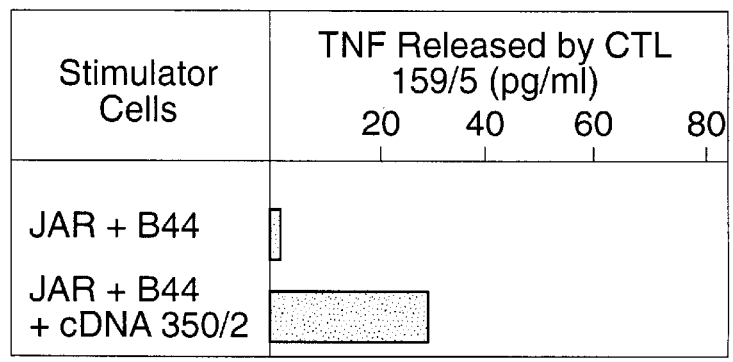

In order to confirm the results obtained to this point, the human choriocarcinoma cell line JAR, which is readily available from the American Type Culture Collection, was used. This cell line does not express HLA molecules, nor is it recognized by CTL 159/5. When JAR was transfected with HLA-B44 cDNA, it was still not recognized by CTL 159/5. Co-transfection with HLA-B44 and 350/2 cDNAs, however, led to lysis, as is seen in FIG. 4B.

The plasmid from the positive clone was removed, and sequenced following art known techniques. Information is showed that the plasmid insert was 1896 base pairs long, and showed no homology with any sequences in data banks. The nucleotide sequence is set forth herein as SEQ ID NO: 1.

EXAMPLE 6

Figure 5A:
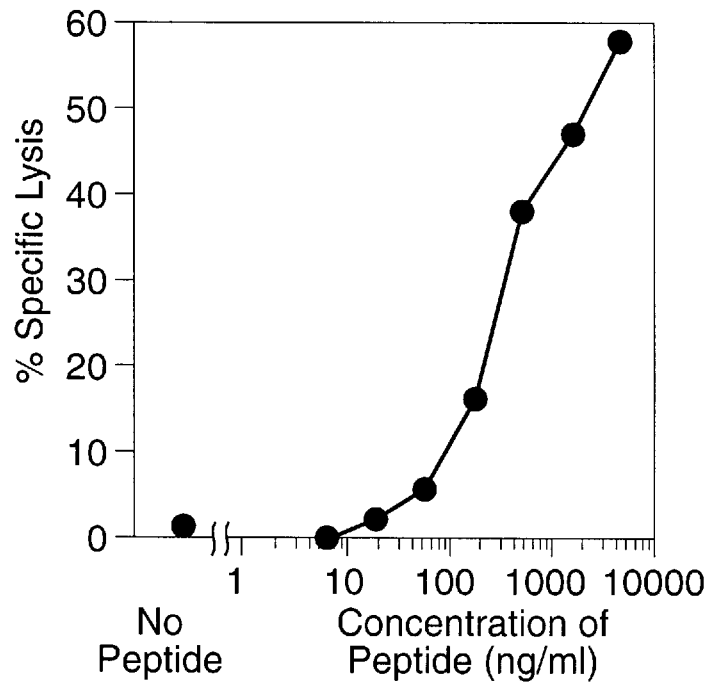
FIG. 5A depicts $^{51}$Cr release in EBV-B cells, when contacted with CTL 159/5.
Figure 5B:
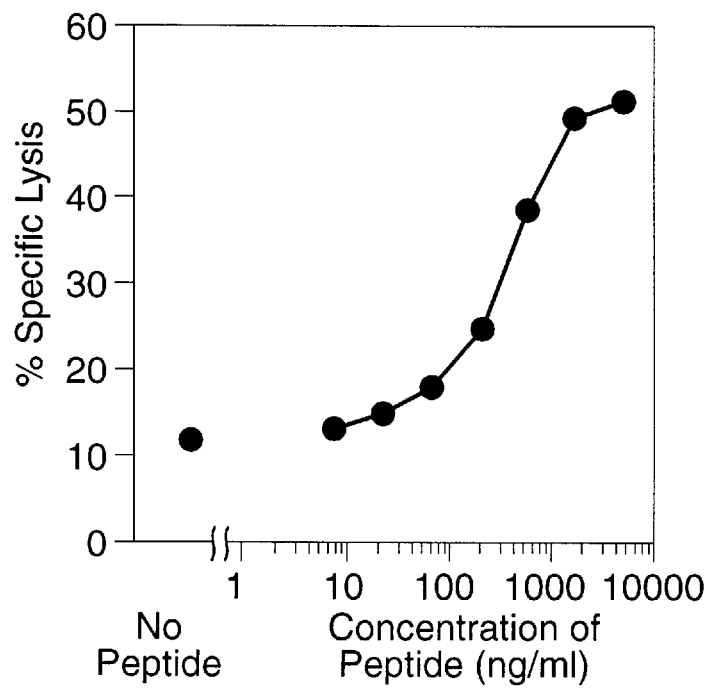
FIG. 5B is similar, but uses LB33-MEL B⁻ cells. In each of FIGS. 5A and 5B, the antigenic peptide of the invention was contacted to the cells prior to contact with the CTLs.

In order to ascertain the peptide which was the tumor rejection antigen, fragments of SEQ ID NO: 1, averaging about 300 base pairs, were amplified via PCR, cloned into pcDNAI/Amp, and then cotransfected into COS cells with plasmid encoding HLA-B44, following the protocols of the preceding examples. These experiments led to identifying the region corresponding to amino acid residues 683–955 of SEQ ID NO: 1 as encoding the antigenic peptide. This region was compared to the peptide described by Khanna, et al., J. Exp. Med. 176: 169–176 (7/92), and the peptide described in Ser. No. 08/233,305, filed Apr. 26, 1994, i.e.:

Glu Glu Lys Leu Ile Val Val Leu Phe corresponds to these residues. As such, a peptide corresponding to this sequence was synthesized, and used to sensitize HLA-B44+ cell lines. The results are shown in FIGS. 5A and 5B, which depict the results of a $^{51}$Cr release assay using EBV transformed B cells (FIG. 6A), and the B− variant described supra (FIG. 6B). The cells were incubated with varying concentrations of the peptide for 30 minutes at 37° C., before adding CTL 159/5 (effector/target ratio: 10:1). Half maximal lysis was obtained with 100–200 ng/ml of peptide.

The foregoing experiments describe isolated nucleic acid molecules coding for a tumor rejection antigen precursor, a "TRAP" molecule. The protein molecule for which these code is processed intracellularly in a manner which leads to production of at least one tumor rejection antigen, or "TRA", which is presented by HLA-B44 molecules. While it has been observed previously that HLA-B44 molecules present peptides derived from tyrosinase, the nucleic acid molecules of the invention do not code for tyrosinase, and the TRAs are not tyrosinase derived.

The tumor rejection antigens of the invention are isolated nonapeptides which have a Glu residue at the 2nd position, and a Phe residue at the 9th position. Especially preferred is the nonamer of SEQ ID NO: 2, i.e.:

Glu Glu Lys Leu Ile Val Val Leu Phe.

Also useful are nonapeptides which, in addition to the required residues at positions 2 and 9, have one or more of the following defined residues:

position 1: Glu
position 3: Lys
position 4: Leu
position 5: Ile
position 6: Val
position 7: Val
position 8: Leu The peptides of the invention are similar to the peptide disclosed in Ser. No. 08/233,305, so-assigned to the assignee of the subject application, i.e.:

Ser Glu Ile Trp Arg Asp Ile Asp Phe (SEQ ID NO: 3)

Khanna, et al., supra, teaches a decamer, i.e.:

Glu Glu Asn Leu Leu Asp Phe Val Arg Phe (SEQ ID NO: 4)

but does not discuss how modification of the decamer could lead to an effective nonamer.

The invention thus involves isolated nucleic acid molecules which code for a tumor rejection antigen precursor, or "TRAP", with the proviso that the TRAP is not tyrosinase such as, but not being limited to, SEQ ID NO: 1 and nucleic acid molecules which code for a tumor rejection antigen precursor processed to at least one antigen presented by HLA-B44, which hybridize to the molecules of SEQ ID NO: 1 under stringent conditions, such as 3.5×SSC, 1×Denhardt's solution, 25 mM sodium phosphate buffer (pH 7.0), 0.5% SDS, and 2 mM EDTA for 18 hours, followed by four washes at 65° C. for 20 minutes in 2×SSC, 0.1% SDS, and one wash of up to 20 minutes in 0.5×SSC, 0.1% SDS. Other conditions, reagents, and so forth will result in the same, or greater stringency, as one of ordinary skill in the art will know. The TRAP coded for is one which is processed to at least one tumor rejection antigen, or TRA, which is presented by HLA-B44 molecules on cell surfaces. The nucleic acid molecules of the invention may be, e.g., genomic DNA, ("gDNA"), complementary DNA ("cDNA"), or a form of RNA. The invention also involves isolated nucleic acid molecules which are complementary to the molecules described above. An especially preferred form of the invention are molecules which contain the sequence set forth in SEQ ID NO: 1.

Also encompassed by the invention are vectors which contain the nucleic acid molecules of the invention, operably linked to a promoter. The vectors may also include a molecule coding for HLA-B44. As these two molecules, i.e., HLA-B44 and the TRAP, are necessary to generate a cytolytic T cell response, the invention also encompasses expression systems where nucleic acid molecules coding for TRAP and for HLA-B44 are presented as separate portions in, e.g., a kit. The invention also encompasses cell lines transfected by the vectors described herein,.be these prokaryotic cells, such as E. coli, or eukaryotic cells, such as Chinese hamster ovary ("CHO") or COS cells.

As indicated, the complexes of TRA and HLA-B44 provoke a cytolytic T cell response, and as such isolated complexes of the tumor rejection antigen and an HLA-B44 molecule are also encompassed by the invention, as are isolated tumor rejection antigen precursors coded for by the previously described nucleic acid molecules.

The invention as described herein has a number of uses, some of which are described herein. First, the identification of a tumor rejection antigen which is specifically presented by HLA-B44 molecules, as well as a nucleic acid molecule coding for its parallel tumor rejection antigen precursor permits the artisan to diagnose a disorder characterized by expression of the TRAP. These methods involve determining expression of the TRAP gene, and/or TRAs derived therefrom, such as TRA presented by HLA-B44. Other TRAs may also be derived from the TRAPs of the invention and presented by different HLA molecules. In the former situation, such determinations can be carried out via any standard nucleic acid determination assay, including the polymerase chain reaction, or assaying with labelled hybridization probes. In the latter situation, assaying with binding partners for complexes of TRA and HLA, such as antibodies, is especially preferred.

The isolation of the TRAP gene also makes it possible to isolate the TRAP molecule itself, especially TRAP molecules containing the amino acid sequence of SEQ ID NO: 1. Fragments of peptides of these isolated molecules when presented as the TRA, or as complexes of TRA and HLA, such as HLA-B44, may be combined with materials such as adjuvants to produce vaccines useful in treating disorders characterized by expression of the TRAP molecule. In addition, vaccines can be prepared from cells which present the TRA/HLA complexes on their surface, such as non-proliferative cancer cells, non-proliferative transfectants, etcetera. In all cases where cells are used as a vaccine, these can be cells transfected with coding sequences for one or both of the components necessary to prove a CTL response, or be cells which express both molecules without transfection. Further, the TRAP molecule, its associated TRAs, as well as complexes of TRA and HLA, may be used to produce antibodies, using standard techniques well known to the art.

When "disorder" is used herein, it refers to any pathological condition where the tumor rejection antigen precursor is expressed. An example of such a disorder is cancer, melanoma in particular.

Therapeutic approaches based upon the disclosure are premised on a response by a subject's immune system, leading to lysis of TRA presenting cells, such as HLA-B44 cells. One such approach is the administration of CTLs specific to the complex to a subject with abnormal cells of the phenotype at issue. It is within the skill of the artisan to develop such CTLs in vitro. Specifically, a sample of cells, such as blood cells, are contacted to a cell presenting the complex and capable of provoking a specific CTL to proliferate. The target cell can be a transfectant, such as a COS cell of the type described supra. These transfectants present the desired complex on their surface and, when combined with a CTL of interest, stimulate its proliferation. COS cells, such as those used herein are widely available, as are other suitable host cells.

To detail the therapeutic methodology, referred to as adoptive transfer (Greenberg, J. Immunol. 136(5): 1917 (1986); Reddel et al., Science 257: 238 (Jul. 10, 1992); Lynch et al., Eur. J. Immunol. 21: 1403–1410 (1991), Kast et al., Cell 59: 603–614 (Nov. 17, 1989)), cells presenting the desired complex are combined with CTLs leading to proliferation of the CTLs specific thereto. The proliferated CTLs are then administered to a subject with a cellular abnormality which is characterized by certain of the abnormal cells presenting the particular complex. The CTLs then lyse the abnormal cells, thereby achieving the desired therapeutic goal.

The foregoing therapy assumes that at least some of the subject's abnormal cells present the HLA/TRA complex. This can be determined very easily, as the art is very familiar with methods for identifying cells which present a particular HLA molecule, as well as how to identify cells expressing DNA containing the indicated sequences. Once isolated, such cells can be used with a sample of a subject's abnormal cells to determine lysis in vitro. If lysis is observed, then the use of specific CTLs in such a therapy may alleviate the condition associated with the abnormal cells. A less involved methodology examines the abnormal cells for HLA phenotyping, using standard assays, and determines expression via amplification using, e.g., PCR.

Adoptive transfer is not the only form of therapy that is available in accordance with the invention. CTLs can also be provoked in vivo, using a number of approaches. One approach, i.e., the use of non-proliferative cells expressing the complex, has been elaborated upon supra. The cells used in this approach may be those that normally express the complex, such as irradiated melanoma cells or cells transfected with one or both of the genes necessary for presentation of the complex. Chen et al., Proc. Natl. Acad. Sci. USA 88: 110–114 (January, 1991) exemplifies this approach, showing the use of transfected cells expressing HPVE7 peptides in a therapeutic regime. Various cell types may be used. Similarly, vectors carrying one or both of the genes of interest may be used. Viral or bacterial vectors are especially preferred. In these systems, the gene of interest is carried by, e.g., a Vaccinia virus or the bacteria BCG, and the materials de facto "infect" host cells. The cells which result present the complex of interest, and are recognized by autologous CTLs, which then proliferate. A similar effect can be achieved by combining the tumor rejection antigen or the precursor itself with an adjuvant to facilitate incorporation into HLA-B44 presenting cells which present the HLA molecule of interest. The TRAP is processed to yield the peptide partner of the HLA molecule while the TRA is presented without the need for further processing.

Other aspects of the invention will be clear to the skilled artisan and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

We claim:

1. An isolated cytolytic T cell which is specific for complexes of an HLA-B44 molecule and a nonapeptide consisting of the amino acid sequence:

Glu Glu Lys Leu Ile Val Val Leu Phe (SEQ ID NO: 2).

* * * * *

SEQUENCE LISTING ( 1 ) GENERAL INFORMATION:

( i i i ) NUMBER OF SEQUENCES: 9

( 2 ) INFORMATION FOR SEQ ID NO:1:

( i ) SEQUENCE CHARACTERISTICS:
        ( A ) LENGTH: 1896 base pairs
        ( B ) TYPE: nucleic acid
        ( C ) STRANDEDNESS: single
        ( D ) TOPOLOGY: linear ( x i ) SEQUENCE DESCRIPTION: SEQ ID NO: 1:

```
GCGGCGGTGG  CGGAGGCGGA  CACATTGGCG  TGAGACCTGG  GAGTACGTTG  TGCCAAATCA      60
TTGCCACTTG  CCACATGAGT  GTAAATGATG  GCGGATGCAA  GTATGTCCTC  TGCCGATGGG     120
AAAAGCGATT  ATGGCCTGCG  AAGGTGACAG  CCATTATTCT  GTAACTTCAG  GACTTAGAAA     180
TGACTTTCGG  GTGACAAGTA  AAATCTTGAT  CAGGAGATAC  CTAGGATTTG  CTTCAGTGAA     240
ATAATTGAGC  CAGAACACGG  TTGGCACTGA  TTCTCGTTCC  CCATTTAATG  GGGTTTTGGT     300
CTAGTGCTTC  CAAGGTTACA  CTTCCAGAAA  TGTCTTTTTT  TTTTCACACT  AAAAAAAAAA     360
AAAAGAATCA  GCTGTAAAAA  GGCATGTAAG  GCTGTAACTC  AAGGAAAGAT  CTGGCAAGCA     420
GCCCTGTGAT  AGTAAATTAT  GGTCGTGTTC  AGGGAATGCT  TTCCAGCAAT  TCAGTAGACA     480
GTGCTCAGCT  GCAATGCAAA  AGCCCAGGTC  CTTGTCTTTG  TCTGCCACTG  GCCTCTCATG     540
CCTCAGTTTC  CCCATCTGTG  AAACAATGGG  GATTGGACCA  AATATCTGAA  ATCCCATGGT     600
TATAGGCCTT  CAGGATTACC  TGCTGCATTT  GTGCTAAAGT  TTGCCACTGT  TTCTCACTGT     660
CAGCTGTTGT  AATAACAAGG  ATTTTCTTTT  GTTTAAATG   TAGGTTTTGG  CCCGAACCGC     720
GACTTCAACA  AAAAATAAGA  GAAGAAAGGA  ATATTTCTA   GCTGTGCAAA  TCCTCTCCCT     780
AGAGGAAAAG  TTAATTGTTG  TGTTGTTTTA  ATACTGTTTT  TTCCCGTGTA  GATTTCTGAT     840
ACTTCAATCC  CCTACTCCCC  CAAAACAGTT  GAAGCCCAGC  CCACTCTTAA  TGGGCTTATT     900
CACCATTTGT  GTAATTCATT  AATGCTCATA  ATAACCTCAT  GAGAAAGCAA  CTAGTTTGAT     960
TTTATGTCAG  TTTGGAAGCT  GAAGATCCAA  ACGAGGCATT  CTGTGAGATC  TATGGAGAGA    1020
TTGGTACAAA  CACTGAATAC  ATGTAAATTA  TACTCAGGGT  AGACCCTATT  TGTGGTTAAA    1080
ATAGGGATAT  TTCCTTTTTT  TTTTTTTTT   TTTTGACTGT  TTCTTAATCA  GTGCCATGCC    1140
AGGAAAATAG  GGATGTTTCC  TTCCCAGAGA  TCTGTGTGTC  TTTTTTCAGA  AACGTCTGTG    1200
ACAGGCCCAT  CAATTTTGAA  ATATTTGGTT  TTTGAGCCTG  TCACTCTAAA  CCAGCGTTTA    1260
ACGTTCAAAA  GGCAAATAAC  TGATGACCAG  GCGGCACATT  GTTCTGCTCC  GTGAGTGTCT    1320
GGCACTGGGA  AAGGTGTAGA  TTGTCTAGAA  TGACAGCAAT  TCCGACGCCC  CAGTCAGTCC    1380
TGCGTGATTG  TGGCGAGGGC  GCGTCTGGCA  CCGGGAAGGT  GTAGATCATC  TAGAATGACG    1440
GCGATTCCGA  CGCCCCGGTC  AGTCCTGCGT  GATTGGCGAG  GGTGCATCTG  TCGTGAGAAT    1500
TCCCAGTTCT  GAAGAGAGCA  AGGAGACTGA  TCCCGCGTAG  TCCAAGGCAT  TGGCTCCCCT    1560
GTTGCTCTTC  CTTGTGGAGC  TCCCCCTGCC  CCACTCCCTC  CTGCCTGCAT  CTTCAGAGCT    1620
GCCTCTGAAG  CTCGCTTGGT  CCCTAGCTCA  CACTTTCCCT  GCGGCTGGGA  AGGTAATTGA    1680
ATACTCGAGT  TTAAAAGGAA  AGCACATCCT  TTTAAACCAA  AACACACCTG  CTGGGCTGTA    1740
AACAGCTTTT  AGTGACATTA  CCATCTACTC  TGAAAATCTA  ACAAGGAGT   GATTTGTGCA    1800
GTTGAAAGTA  GGATTTGCTT  CATAAAAGTC  ACAATTTGAA  TTCATTTTTG  CTTTTAAATC    1860
```

CAGCCAACCT TTTCTGTCTT AAAAGGAAAA AAAAAA                1896

( 2 ) INFORMATION FOR SEQ ID NO:2:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 2:

Glu Glu Lys Leu Ile Val Val Leu Phe
              5

( 2 ) INFORMATION FOR SEQ ID NO:3:

( i ) SEQUENCE CHARACTERISTICS:
        ( A ) LENGTH: 9 amino acid residues
        ( B ) TYPE: amino acid
        ( D ) TOPOLOGY: linear ( x i ) SEQUENCE DESCRIPTION: SEQ ID NO: 3:

Ser Glu Ile Trp Arg Asp Ile Asp Phe
              5

( 2 ) INFORMATION FOR SEQ ID NO:4:

( i ) SEQUENCE CHARACTERISTICS:
        ( A ) LENGTH: 10 amino acid residues
        ( B ) TYPE: amino acid
        ( D ) TOPOLOGY: linear ( x i ) SEQUENCE DESCRIPTION: SEQ ID NO: 4:

Glu Glu Asn Leu Leu Asp Phe Val Arg Phe
            5              10

( 2 ) INFORMATION FOR SEQ ID NO:5:

( i ) SEQUENCE CHARACTERISTICS:
        ( A ) LENGTH: 9 amino acid residues
        ( B ) TYPE: amino acid
        ( D ) TOPOLOGY: linear ( i x ) FEATURE:
        ( D ) OTHER INFORMATION: Each Xaa is any amino acid ( x i ) SEQUENCE DESCRIPTION: SEQ ID NO: 5:

Xaa Glu Lys Xaa Xaa Xaa Xaa Xaa Phe
              5

( 2 ) INFORMATION FOR SEQ ID NO:6:

( i ) SEQUENCE CHARACTERISTICS:
        ( A ) LENGTH: 9 amino acid residues
        ( B ) TYPE: amino acid
        ( D ) TOPOLOGY: linear ( i x ) FEATURE:
        ( D ) OTHER INFORMATION: Each Xaa is any amino acid ( x i ) SEQUENCE DESCRIPTION: SEQ ID NO: 6:

Xaa Glu Xaa Xaa Ile Xaa Xaa Xaa Phe
              5

( 2 ) INFORMATION FOR SEQ ID NO:7:

( i ) SEQUENCE CHARACTERISTICS:
        ( A ) LENGTH: 9 amino acid residues
        ( B ) TYPE: amino acid
        ( D ) TOPOLOGY: linear ( i x ) FEATURE:
    ( D ) OTHER INFORMATION: Each Xaa is any amino acid ( x i ) SEQUENCE DESCRIPTION: SEQ ID NO: 7:

Xaa Glu Xaa Xaa Xaa Val Xaa Xaa Phe
                5

( 2 ) INFORMATION FOR SEQ ID NO:8:

( i ) SEQUENCE CHARACTERISTICS:
    ( A ) LENGTH: 9 amino acid residues
    ( B ) TYPE: amino acid
    ( D ) TOPOLOGY: linear ( i x ) FEATURE:
    ( D ) OTHER INFORMATION: Each Xaa is any amino acid ( x i ) SEQUENCE DESCRIPTION: SEQ ID NO: 8:

Xaa Glu Xaa Xaa Xaa Xaa Val Xaa Phe
                5

( 2 ) INFORMATION FOR SEQ ID NO:9:

( i ) SEQUENCE CHARACTERISTICS:
    ( A ) LENGTH: 9 amino acid residues
    ( B ) TYPE: amino acid
    ( D ) TOPOLOGY: linear ( i x ) FEATURE:
    ( D ) OTHER INFORMATION: Each Xaa is any amino acid ( x i ) SEQUENCE DESCRIPTION: SEQ ID NO: 9:

Xaa Glu Xaa Xaa Xaa Xaa Xaa Leu Phe
                5